United States Patent [19]

Kato

[11] Patent Number: 4,655,572

[45] Date of Patent: Apr. 7, 1987

[54] CAMERA DEVICE FOR ENDOSCOPE

[75] Inventor: Shinichi Kato, Tokyo, Japan

[73] Assignee: Olympus Optical Co., Ltd., Tokyo, Japan

[21] Appl. No.: 763,977

[22] Filed: Aug. 9, 1985

[30] Foreign Application Priority Data

Aug. 17, 1984 [JP] Japan ............................ 59-171224

[51] Int. Cl.⁴ .................... G03B 1/18; G03B 1/60; G03B 37/00; G03B 17/00
[52] U.S. Cl. .................... 354/173.11; 354/62; 354/218; 354/289.1; 354/475
[58] Field of Search ............... 354/62, 63, 217, 218, 354/173.1, 173.11, 410, 289, 475

[56] References Cited

U.S. PATENT DOCUMENTS

| | | | |
|---|---|---|---|
| 3,816,842 | 6/1974 | Glaros et al. | 354/218 X |
| 4,343,300 | 8/1982 | Hattori | 354/62 X |
| 4,373,796 | 2/1983 | Matsura et al. | 354/173.1 |
| 4,383,746 | 5/1983 | Aratame | 354/173.1 |
| 4,423,938 | 1/1984 | Tominaga | 354/289.1 X |
| 4,461,560 | 7/1984 | Yoshino et al. | 354/217 X |
| 4,482,227 | 11/1984 | Shiozawa et al. | 354/173.11 |
| 4,500,183 | 2/1985 | Tanikawa | 354/217 X |

FOREIGN PATENT DOCUMENTS

| | | |
|---|---|---|
| 53-11020 | 2/1978 | Japan . |
| 56-24330 | 3/1981 | Japan . |
| 56-24333 | 3/1981 | Japan . |
| 57-130828 | 8/1982 | Japan . |

*Primary Examiner*—Donald A. Griffin

[57] ABSTRACT

A camera device for an endoscope comprises a character display section for displaying data relative to an endoscopic image, and drive motors for film winding and shutter drive. The camera device further comprises a sensor for detecting a residual film quantity corresponding to a predetermined number of frames or less, a sensor for detecting the film end, and sensors for detecting a malfunction of the drive motors. Detection data detected by these sensors are displayed by the display section.

13 Claims, 5 Drawing Figures

CAMERA DEVICE FOR ENDOSCOPE

BACKGROUND OF THE INVENTION

The present invention relates to a camera device for an endoscope, and more specifically to a camera device for an endoscope having a display section within the field of view of a view finder.

Cameras for endoscopes are attached to an endoscope to serve in endoscopic image photographing. Although provided with a character display section for displaying data relative to an endoscopic image, such as date, patient name, etc., and an EE level display segment, these cameras have no function by which to display either a residual film quantity or a malfunction of the camera drive mechanism. During a photography session, therefore, the operator is entirely unaware of such vital information as completion of the film's total number of exposures, insufficient film advance, or wrong shutter operation, if any, thus severely limiting the operations capacity to ensure a high quality of photographic imaging.

SUMMARY OF THE INVENTION

The object of the present invention is to provide a camera for an endoscope capable of displaying the film condition or a malfunction of the camera drive mechanism.

According to the present invention, there is provided a camera device adapted for use with an endoscope, comprising a character display section capable of displaying data relative to an endoscopic image, motors for winding a film and driving a shutter, a sensor for detecting a residual film quantity equivalent to a predetermined number of frames or less, a sensor for detecting the film end and a circuit for urging the display section to display detection information detected by the sensors.

DETAILED DESCRIPTION OF THE PREFERRED EMBODIMENT

Figure 1:
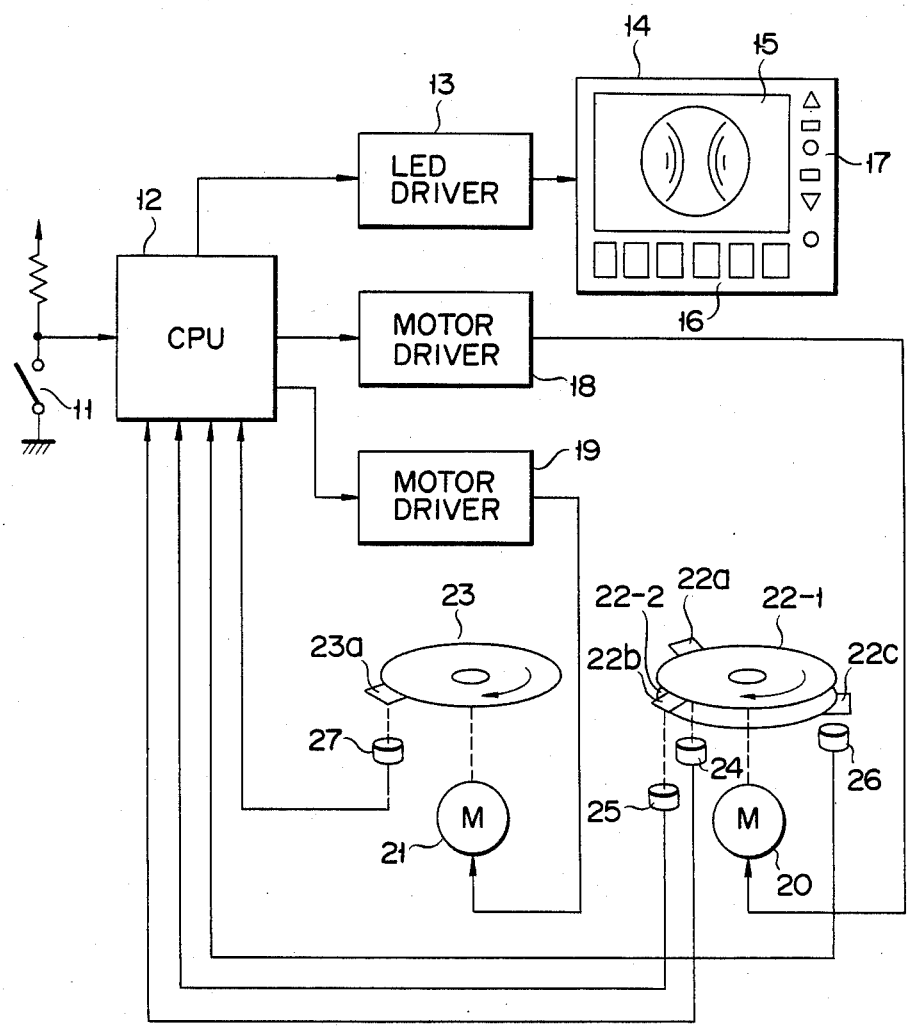
FIG. 1 is a schematic block circuit diagram of a camera device for an endoscope according to an embodiment of the present invention.

Referring now to FIG. 1, there is shown a camera device according to one embodiment of the present invention, in which a release switch 11 is connected to a CPU 12 for general control of the camera. The CPU 12 is connected to a finder unit 14 through an LED driver 13. The finder unit 14 includes a finder screen 15 on which is projected an endoscopic image transmitted through the image guide of an endoscope (not shown), a character display section 16 provided under the finder section 15, and an EE level display segment 17 at one side of the finder screen 15. The CPU 12 is connected to motors 20 and 21 through motor drivers 18 and 19, respectively. The motor 20, which serves in film winding, is coupled with, for example, rotary disks 22-1 and 22-2 which rotate in association with the motor 20. The rotary disk 22-1 is designed so as to rotate by one step each time the film is advanced one frame, while the rotary disk 22-2 is adapted to make a full turn while the motor 20 makes revolutions required for winding the film. The rotary disk 22-1 is fitted with reflecting plates 22a and 22b, and the rotary disk 22-2 with a single reflecting plate 22c. Photosensors 24, 25 and 26 are arranged so as to be able to detect the reflecting plates 22a, 22b and 22c, respectively. The photosensor 24 is intended to detect that the remaining or unexposed frames are few, e.g., five or less in number, while the photosensor 25 serves to detect the film end. The photosensor 26 serves to detect start and end of operation of the motor 20.

The motor 21, which is provided for driving the mirror shutter of the camera, is coupled with, for example, a rotary disk 23 which rotates in association with the motor 21. The rotary disk 23 is also fitted with a reflecting plate 23a. A photosensor 27 is provided for detecting the reflecting plate 23a. By sensing the reflecting plate 23a, the photosensor 27 detects the start or end of operation of the motor 21.

Figure 2:
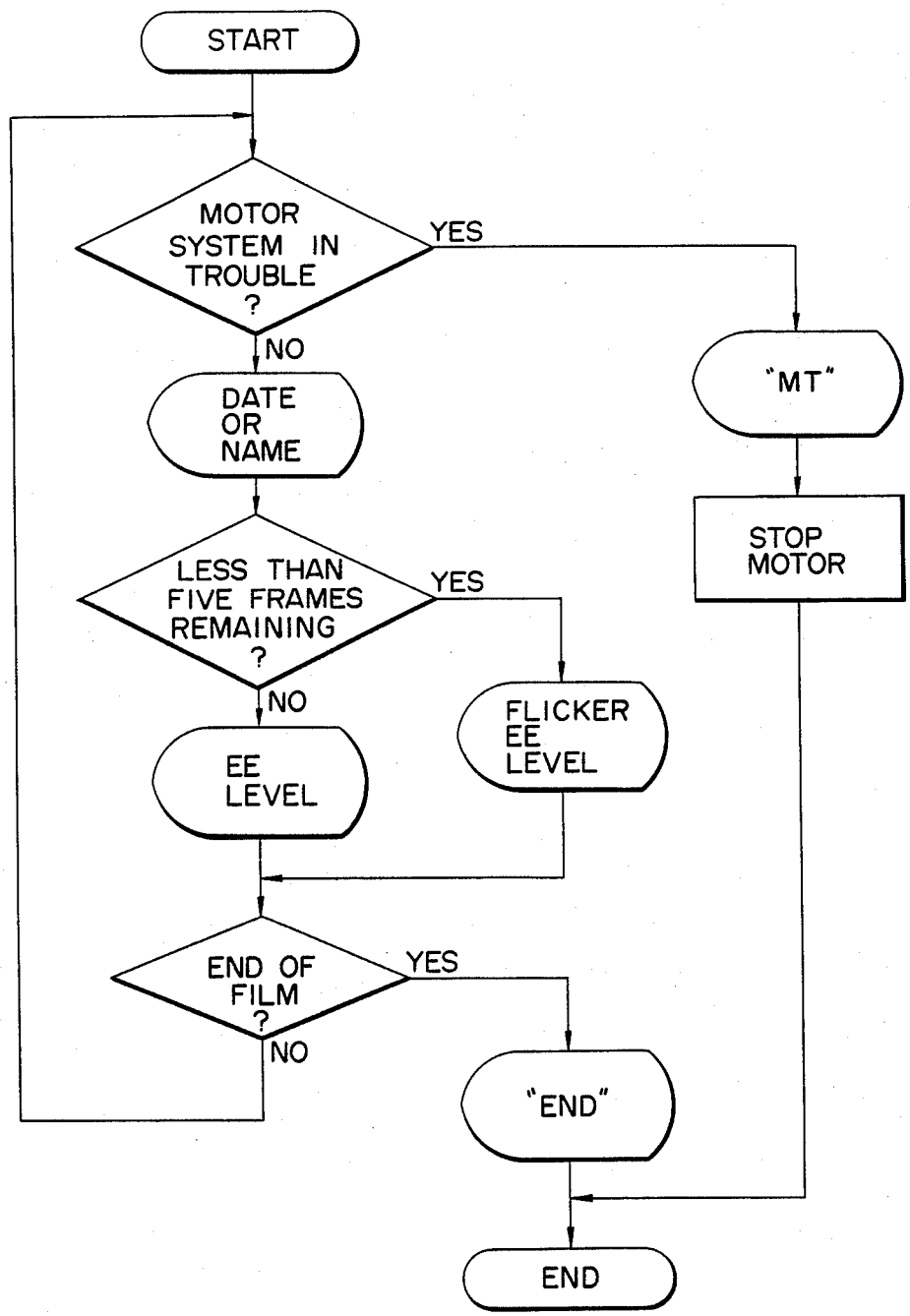
FIG. 2 is a flow chart for illustrating the operation of the circuit shown in FIG. 1.

Referring now to the flow chart of FIG. 2, the operation of the aforementioned camera for endoscope will be described.

When the camera is mounted on the eyepiece section of the endoscope, the CPU 12 gives an operating instruction to the motor drivers 18 and 19, thereby starting the motors 20 and 21. As the motors 20 and 21 are rotated in this manner, the rotary disks 22-1, 22-2 and 23 rotate correspondingly. The photosensors 26 and 27 detect the reflecting plates 22c and 23a as they rotate with the rotary disks 22-1 and 23, respectively. On detecting the reflecting plates 22c and 23a, the photosensors 26 and 27 supply the CPU 12 with signals responsive to the start and end of rotation of the motors 20 and 21. The CPU 12 then determines the normality of the motor drive system by the time interval between the start and end of motor drive. Namely, if either motor is slowed down or stopped by an extraordinary load, contact error or disconnection without causing the CPU 12 to receive a motor stop signal within a predetermined time after reception of a motor start signal, then the CPU 12 concludes that the motor drive system is subject to a malfunction. In such a case, the CPU 12, through the LED driver 13, causes the character display section 16 to display "MT" which is indicative of a malfunction.

If the motor drive system is normal, the character display section 16 displays regular data including date, patient name, etc. These regular data are inputted by means of data input keys (not shown) arranged on the camera or a data input unit (not shown). Then, whether or not the remaining frames are five or below in number is determined in accordance with the output signal of the photosensor 24. If the remainder is found to be five or less, the CPU 12 urges the LED driver 13 to flicker the EE level display segment 17. Then, the CPU 12 determines whether or not the film end is reached in accordance with the output signal of the photosensor 25. If the film end is not detected, the first step of the operation sequence is resumed. Thereafter, the abovementioned processes of operation are repeated. When the film end is reached, the CPU 12, through the LED driver 13, urges the character display section 16 to display "END" which is indicative of the film end. Thereupon, the whole operation sequence is ended.

According to the present invention, as described above, the character display section and EE level display segment, which normally display data on the patient or the like, can indicate a malfunction of the motor drive system, film end and/or warning of film end. Thus, in accordance with these indications, the operator can immediately cope with any trouble in the camera or regarding the film condition, thereby avoiding failures in photographing. The character display section may display the number of film-frames. In this case, the CPU 12 counts up each time the film is advanced one frame and supplies the count valve to the LED driver 13.

Figure 3:
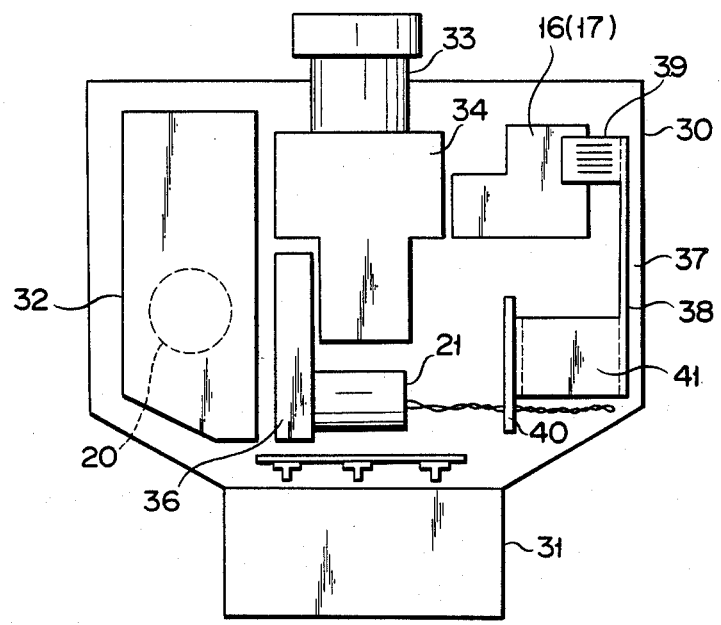
FIG. 3 is a plan view of an endoscopic camera of the camera device.
Figure 4:
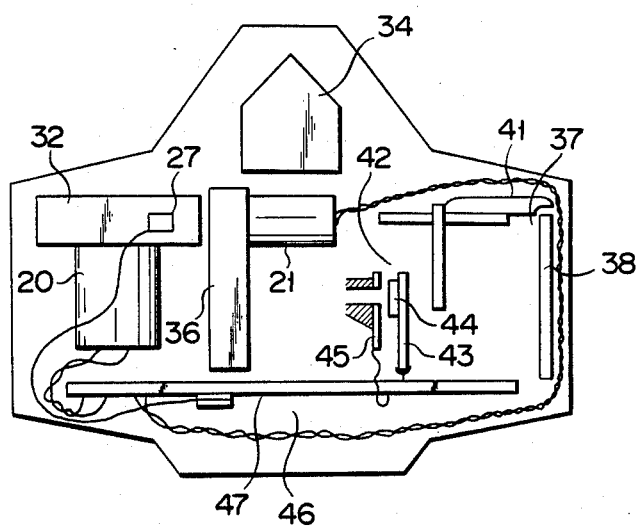
FIG. 4 is a front view of the camera of FIG. 3.
Figure 5:
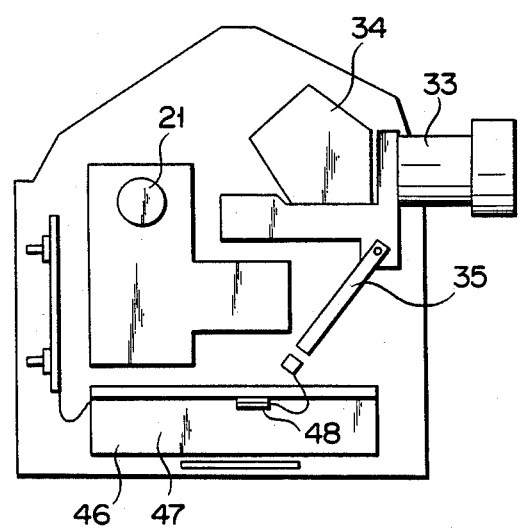
FIG. 5 is a side view of the camera of FIG. 3.

FIGS. 3 to 5 show a specific arrangement of the above described camera for endoscope. According to this arrangement, the eyepiece section of an endoscope (not shown) is connected to a connecting section 31 in front of a camera body 30. The film winding motor 20 is disposed on one side (left-hand side in FIG. 3) of the camera body 30, where said film winding motor 20 is coupled to a film winding mechanism block 32. The film winding mechanism block 32 contains a gear mechanism, the rotary disks 22-1 and 22-2, the reflecting plates 22a, 22b and 22c, and the photosensors 24, 25 and 26.

A loupe block 33 is attached to the central portion of the back of the camera body 30. The loupe block 33 is optically coupled to a mirror block 34, and a movable mirror 35 is disposed on the optical axis of the mirror block 34. A mirror drive block 36 adjoins the movable mirror 35. The mirror drive block 36, which is coupled to the mirror drive motor 21, is provided with a gear mechanism for transmitting motor drive force, and a return mechanism for returning the moved mirror, as well as with the rotary disk 23, the reflecting plate 23a, and the photosensor 27.

A substrate block 37 is disposed in a portion on the right side of the camera body 30. The substrate block 37 includes a control substrate 38 which incorporates an electronic circuit for EE control and data superimposition control. The control substrate 38 is connected with the character display section 16 and the EE level display segment 17 by means of a flexible substrate 39, and with a data superimposition LED 40 by means of another flexible substrate 41.

A photometric block 42 which is disposed close to the optical path inside the camera body 30, includes an electronic circuit substrate 43 which bears a light receiving element 44 and other electronic circuit components required for photometry. An iris diaphragm 45 is provided in front of the light receiving element 44.

An electrical block 46 is provided at a portion on the bottom of the camera body 30. The electrical block 46 includes an electrical substrate 47 which bears electronic components for controlling the film winding mechanism block 32, the mirror drive block 36, and the substrate block 37. The electrical substrate 47 is connected with a sensor 48 for sensing the rocking motion of the movable mirror 35.

What is claimed is:

1. A camera device adapted for use with an endoscope, comprising:
character display means for displaying character data relative to an endoscopic image; a drive section for winding a film and driving a shutter; means for detecting a residual film quantity equivalent to a predetermined number of frames or less, in order to output detection information; means for detecting the film end, in order to output detection information; means for detecting a malfunction of the drive section, in order to output detection information; and means for causing said character display means to display the character data relative to the endoscopic image, when the camera device is functioning normally, and to display the detection information detected by at least one of the detecting means, in the case of malfunctioning of said camera device.

2. The camera device according to claim 1, wherein said drive section includes a first motor for film winding and a second motor for shutter drive, and said residual film quantity detecting means includes a rotating member adapted to rotate in association with the first motor and by one step each time the film is advanced one frame, and means for detecting the position of the rotating member corresponding to the predetermined frame number.

3. The camera device according to claim 1, wherein said predetermined frame number is five.

4. The camera device according to claim 1, wherein said drive section includes a first motor for film winding and a second motor for shutter drive, and said film end detecting means includes a rotating body adapted to rotate in association with the first motor and by one step each time the film is advanced one frame, and means for detecting the position of the rotating member corresponding to the film end.

5. The camera device according to claim 1, wherein said drive section includes a first motor for film winding and a second motor for shutter drive, and said drive section malfunction detecting means includes means for detecting the time interval between the start and end of rotation of the motors, determining a possible malfunction of the motors by the detected time interval.

6. A camera device adapted for use with an endoscope, for providing an endoscopic image, and comprising:
a display unit including at least a display means for displaying data relative to the endoscopic image; a drive section for winding a film having a film end and driving a shutter; means for detecting a residual film quantity equivalent to a predetermined number of frames or less, in order to output detection information; means for detecting the film end, in order to output detection information; means for detecting a malfunction of the drive section, in order to output detection information; and means for causing said display means to flicker to indicate a malfunction in response to the detection information detected by at least one of the detecting means.

7. The camera device according to claim 6, wherein said drive section includes a first motor for winding the film and a second motor for driving the shutter, and said residual film quantity-detection means includes a rotating member which rotates in association with said first motor, and which moves by one position each time the film is advanced one frame, and means for detecting the position of said rotating member corresponding to the predetermined frame number.

8. The camera device according to claim 7, wherein said residual film quantity-detection means is means for detecting a residual film quantity equivalent to five frames.

9. The camera device according to claim 6, wherein said drive section includes a first motor for winding the film, and a second motor for driving the shutter, and said film-end detection means includes a rotating member which rotates in association with said first motor, and which moves by one position each time the film is advanced one frame, and means for detecting the position of the rotating member, corresponding to the film end.

10. The camera device according to claim 6, wherein said drive section includes a first motor for winding the film, and a second motor for driving the shutter, and said drive section malfunction detection means includes means for detecting the time interval between the start and end of rotation of said motors, and for determining a possible malfunction of said motors on the basis of the detected time interval.

11. The camera device according to claim 6, wherein said drive section includes a first motor for winding the film, and a second motor for driving the shutter, and said residual film quantity-detection means includes a rotating member which rotates in association with said first motor, and which moves by one position each time the film is advanced one frame, and means for detecting the position of said rotating member, corresponding to the predetermined frame number, and said film-end detection means includes a rotating member which rotates in association with said first motor, and which moves by one position each time the film is advanced one frame, and means for detecting the position of the rotating member, corresponding to the film end.

12. The camera device according to claim 11, wherein said residual film quantity-detection means is means for detecting a residual film quantity equivalent to five frames.

13. The camera device according to claim 6, wherein said drive section includes a first motor for winding the film, and a second motor for driving the shutter, and said residual film quantity-detection means includes a rotating member which rotates in association with said first motor, and which moves by one position each time the film is advanced one frame, and means for detecting the position of said rotating member corresponding to the predetermined frame number, and said film-end detection means includes a rotating member which rotates in association with said first motor, and which moves by one position each time the film is advanced one frame, and means for detecting the position of the rotating member, corresponding to the film end, and said drive section malfunction detection means includes means for detecting the time interval between the start and end of rotation of said motors and for determining a possible malfunction of said motors by the detected time interval.

* * * * *